United States Patent [19]

Wong et al.

[11] Patent Number: 5,976,082
[45] Date of Patent: Nov. 2, 1999

[54] METHOD FOR IDENTIFYING AT RISK PATIENTS DIAGNOSED WITH CONGESTIVE HEART FAILURE

[75] Inventors: Bruce J. O. Wong, Radnor, Pa.; Felix Friedman, Eden Praire, Minn.

[73] Assignee: SmithKline Beecham Corporation, Philadelphia, Pa.

[21] Appl. No.: 08/790,690

[22] Filed: Jan. 29, 1997

Related U.S. Application Data

[60] Provisional application No. 60/019,859, Jun. 17, 1996.

[51] Int. Cl.$^6$ .............................. A61B 5/00; G06F 159/00
[52] U.S. Cl. ............................................................ 600/300
[58] Field of Search ................................... 600/300, 301; 128/920–924

[56] References Cited

U.S. PATENT DOCUMENTS

| | | | |
|---|---|---|---|
| 4,945,476 | 7/1990 | Bodick et al. | 128/923 X |
| 4,991,091 | 2/1991 | Allen | 128/920 X |
| 5,301,105 | 4/1994 | Cummings . | |
| 5,486,999 | 1/1996 | Mebane . | |
| 5,492,117 | 2/1996 | Eisenberg et al. | 600/300 |
| 5,642,936 | 7/1997 | Evans | 128/924 X |

FOREIGN PATENT DOCUMENTS

| | | |
|---|---|---|
| WO 94/04072 | 3/1994 | WIPO . |
| WO 96/13790 | 5/1996 | WIPO . |

OTHER PUBLICATIONS

Woolson, et al., Journal of Methodology, 1980, vol. 19, No. 1, pp. 36–41.
Kendler et al., Amer Journal of Psychiatry, 1993, vol. 150, p1139–48.
Harrison's Principle's of Internal Medicine McGraw–Hill inc Pub 1995, 13 ed. vol. 1, chap 56 & 195.
Parggrey et al. Climical aspect of cardiomyopathy in dialysis, Blood Purif 1994, 12 (4–5); 267–76.
Radermacher et al. treatment or renal anemia by erythropoietin substitution. The effects on the cardiovascular system. Clin Nephrol 1995 44 (Suppl. 1) S56–S60.
Fyhrquist et al. "High serum erythropoietin levels are normal during treatment of congestive heart failure with enalapril." J Intern Med 1989 226 (4): 257–60.
Volpe et al., Blood levels of erythropoietin in congestive heart failure and correlation with clinical, hemodynamic, and hormonal profiles. Sep. 1994 Am J Cardiol 74 (5); 468–473.
J. occup. Med. Mar. 1991, vol. 33, pp. 268–71, J. Med Syst. Feb. 1994, vol. 18 pp. 23–32.
Best review XP 000674874 pp. 50,51,52, 114, Nov. 1989.

*Primary Examiner*—Samuel Gilbert
*Attorney, Agent, or Firm*—James M. Kanagy; Charles Kinzig

[57] ABSTRACT

A computer-implemented technique, including database processing, is used to identify at risk congestive heart failure patients where information about patients exists in a claims database. The technique includes processing the patient information in the claims database to find and extract claims information for a group of congestive heart failure patients. Next, using the extracted information, a set of events, relevant to congestive heart failure, is defined. Next, the extracted information and set of events are processed to create event level information which is organized with respect to events rather than claims. A time window is defined to provide a timeframe from which to judge whether events should be considered in subsequent processing; and, a set of variables is defined as being potential predictors of adverse health outcomes. Subsequently, the event level information, using the time window and the set of variables, is processed to generate an analysis file. Statistical analysis, such as logistic regression, is performed on the analysis file to generate a prediction model where the prediction model is a function of a subset of the set of variables. Finally, the prediction model is applied to the same or another claims database to identify and output at risk patients, diagnosed with congestive heart failure, likely to have adverse health outcomes.

6 Claims, 8 Drawing Sheets

FIG. 2

214
Hospital

Name
Hospital – site code
Physician
Diagnosis
Date
Procedures
length of stay
......

212
Doctor

Name
Physician
diagnosis – ICD-9
Procedures
Date
Amt Claimed
......

210
Rx

Name
date prescribed
Drug code
Amt dispensed
Physician name
Amt claimed
Amt R-reimbursed
......

| EVENT | EVENT DATE | NUMBER | COST | CATEGORY INDICATOR |
|---|---|---|---|---|
| 1. CHF ER | date | NA | $ | NA |
| 2. CHF Hospitalization | date | LOS | $ | NA |
| 3. CHF office visit | date | NA | $ | NA |
| 4. IHD ER | date | NA | $ | subclass |
| 5. IHD Hospitalization | date | LOS | $ | subclass |
| 6. IHD office visit | date | NA | $ | subclass |
| 7. Diabetes ER | date | NA | $ | NA |
| 8. Diabetes Hospitalization | date | LOS | $ | NA |
| 9. Diabetes office visit | date | NA | $ | NA |
| 10. Dysrhythmia ER | date | NA | $ | NA |
| 11. Dysrhythmia Hospitalization | date | LOS | $ | NA |
| 12. Dysrhythmia office visit | date | NA | $ | NA |
| 13. Hypertension ER | date | NA | $ | NA |
| 14. Hypertension Hospitalization | date | LOS | $ | NA |
| 15. Hypertension office visit | date | NA | $ | NA |
| 16. Lifestyle ER | date | NA | $ | NA |
| 17. Lifestyle Hospitalization | date | LOS | $ | NA |
| 18. Lifestyle office visit | date | NA | $ | NA |
| 19. Other Hrt Dz ER | date | NA | $ | NA |
| 20. Other Hrt DZ Hospitalization | date | LOS | $ | NA |
| 21. Other Hrt Dz office visit | date | NA | $ | NA |
| 22. Respiratory ER | date | NA | $ | NA |
| 23. Respiratory Hospitalization | date | LOS | $ | NA |
| 24. Respiratory office visit | date | NA | $ | NA |
| 25. Thyrotoxicosis ER | date | NA | $ | NA |
| 26. Thyrotoxicosis Hospitalization | date | LOS | $ | NA |
| 27. Thyrotoxicosis office visit | date | NA | $ | NA |
| 28. Pulmonary Embolism ER | date | NA | $ | NA |
| 29. Pulmonary Embolism Hosp. | date | LOS | $ | NA |
| 30. Pulmonary Embolism office | date | NA | $ | NA |
| 31. Anemia ER | date | NA | $ | NA |
| 32. Anemia Hospitalization | date | LOS | $ | NA |
| 33. Anemia office visit | date | NA | $ | NA |
| 34. Infection ER | date | NA | $ | NA |
| 35. Infection Hospitalization | date | LOS | $ | NA |
| 36. Infection office visit | date | NA | $ | NA |
| 37. Other ER | date of first | # ER in month | $ | NA |
| 38. Other Hospitalization | date of first | # hosp in month | $ | NA |
| 39. Other office visit | date of first | # OV in month | $ | NA |
| 40. Miscellaneous Medical event | date of first | # in month | $ | # of CV in month |
| 41. Routine CV Procedures | date of first | # on event date | $ | NA |
| 42. Intermediate CV Procedures | date of first | # on event date | $ | NA |
| 43. Critical CV Procedures | date of first | # on event date | $ | NA |
| 44. CV Surgery | date of first | # on event date | $ | NA |
| 45. Rx for ACE inhibitor therapy | date of first | days supply | $ | # rx in month |
| 46. Rx for Loop diuretic therapy | date of first | days supply | $ | # rx in month |
| 47. Rx for other diuretic therapy | date of first | days supply | $ | # rx in month |
| 48. Rx for Digoxin therapy | date of first | days supply | $ | # rx in month |
| 49. Rx for Beta Blocker therapy | date of first | days supply | $ | # rx in month |
| 50. Rx for Ca Channel Blocker tx | date of first | days supply | $ | # rx in month |
| 51. Rx for other CV drug | date of first | days supply | $ | # rx in month |
| 52. Rx for non-CV drug | date of first | days supply | $ | # rx in month |
| 53. Rx for Na/H2O drug | date of first | days supply | $ | # rx in month |

FIG. 4

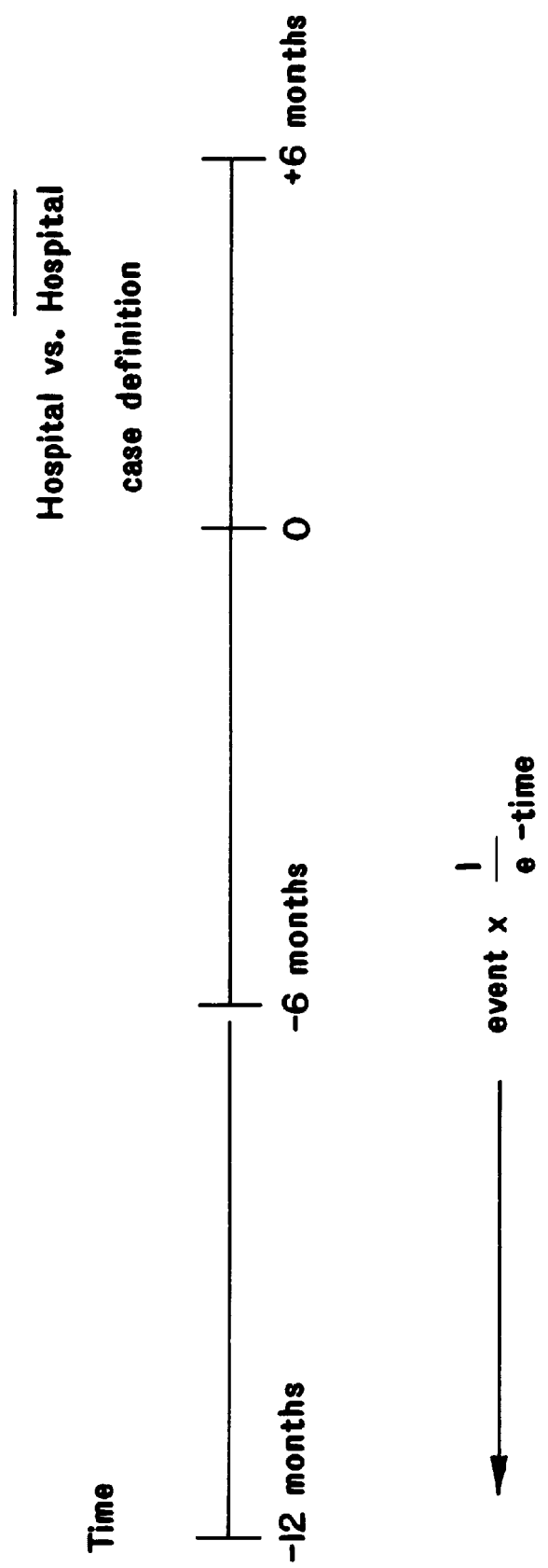

METHOD FOR IDENTIFYING AT RISK PATIENTS DIAGNOSED WITH CONGESTIVE HEART FAILURE

This application claims priority on U.S Provisional application Ser. No. 60/019,859, filed Jun. 17, 1996.

SCOPE OF THE INVENTION

This invention relates to database processing techniques and, more particularly, it relates to identification of congestive heart failure patients having a high risk of adverse health outcomes using various database processing techniques.

BACKGROUND OF THE INVENTION

Congestive heart failure is the symptomatic description of end organ failure of the heart muscle to act as a pump. The failure of the heart to pump blood leads to accumulation of fluid or congestion in the body areas from which the blood was to be pumped. In the case of right ventricular failure, the consequence is systemic edema often manifest initially by symptomatic dependent edema at peripheral sites (e.g. ankles). In the case of left ventricular failure, the fluid accumulation occurs in the lungs and is manifest by pulmonary edema, the primary symptom of which is shortness of breath. Left heart failure is more common and important because of its relative size and the physiologic function of providing systemic circulation to critical organs.

The primary underlying cause of heart failure (low output failure) is coronary artery disease leading to myocardial infarction and cardiac muscle death. Additional pathologies include cardiomyopathies and myocarditis, valvular dysfunction, metabolic and endocrine abnormalities (e.g., hypothyroidism, alcohol, Mg deficiency etc.) pericardial abnormalities.

In 1992, Conjestive Heart Failure (CHF) prevalence was estimated to be approximately 1% of the general population, 6.8% of patients over the age of 65, and 0.2%–0.4% of the managed care population (prior to the active recruiting of senior members). In absolute numbers, this represents approximately 2.76 million patients in the USA. Subclassification by severity provides estimates of 10% as severe, 40% moderate, and the remainder mild. New cases of diagnosed CHF are expected to increase 29%, from 495, 7000 per year in 1992 to 642,000 by the year 2007. This increase can be attributed to several factors, including the general aging of the population, as well as improvements in physician awareness and diagnostic techniques.

There has been a marked increase in the number of seniors enrolling in managed care plans (MCOs). In some plans, seniors can account for up to 50% of total enrollment. In addition, the number of seniors enrolled in Medicare risk programs is projected to grow by 28% to 2.3 million by the end of 1995. Growth in Medicare risk programs is expected to continue, due to the anticipated passage of the Medicare reform bill, which will encourage seniors to join health plans. Also, the current "50/50" provision that forces MCOs to enroll one non-Medicare patient for every Medicare patient enrolled may be overturned, which will make it easy for plans to concentrate on Medicare patients.

Patients with CHF are living longer as treatment options increase. This means that MCOs will need to be able to cost-effectively manage CHF for an ever-growing number of patients. This is made apparent by several other facts. CHF was the most expensive health care problem according to the Healthcare Financing Agency (HCFA) in 1992. Approximately 5.45 billion dollars were spent on hospitalization, or 4.8% of the total Diagnositc Related Group (DRG) budget. CHF is also the single most frequent cause of hospitalization for people age 65 and older. As was previously noted, it is projected that one percent of the general population has CHF, which translates to 6.8% of the elderly. Interestingly, even in MCOs that do not actively recruit seniors, CHF can account for up to 2% of the overall MCO medical loss rate.

Treatment of CHF is primarily symptomatic through three pathophysiologic mechanisms:

1. Afterload reduction—Reduction of the resistance against which the heart must pump blood. Primarily achieved pharmacologically although in severe situations aortic counter pulsation is used.

2. Cardiac Inotropic state—Improvement of the efficiency of the heart through pharmacological agents acting directly on myocardium (e.g. cardiac glycosides), reduction in starling equilibrium's through chamber size reduction and improvement in coronary artery blood flow.

3. Pre-load reduction—Reduction in the volume of blood entering the heart. This can be achieved through pharmacological interventions (diuretics, vasodilators), dietary (salt and water restriction) and physical means (rotating tourniquets, blood volume reduction).

The primary pharmacological interventions, therefore, consist of agents from three primary classes, diuretics, cardiac glycosides and Angiotersin Converting Enzyme (ACE) inhibitors. In addition, recent studies have shown benefit from the use of beta-blockers with anti-oxidant properties. Ultimately, cardiac transplantation now offers an alternative to terminal life threatening heart failure.

The complexity of care required, as outlined above, indicates the need for substantial physician and patient involvement in the optimal management of the condition including the appropriate selection and use of pharmacological interventions and the modification of individual life styles to achieve best results from interventions.

Obviously, an overall objective of any CHF Disease Management Program should be to improve the quality of treatment and outcomes for patients with CHF while, at the same time, achieving cost savings. An important step in doing so is to identify patients who are at high risk of adverse outcomes and assuring "best practice" treatment of these patients. There is, therefore, a real need to identify patients who are at high risk of hospitalization for CHF.

SUMMARY OF THE INVENTION

The present invention involves a computer-implemented method for generating a model to identify at risk patients diagnosed with congestive heart failure, from information about patients existing in a claims database, said method comprising the steps of 1) processing, based on predetermined criteria, the patient information in the claims database to find and extract claims information for a group of congestive heart failure patients; 2) defining, using the information available in the claims database, events relevant to congestive heart failure; 3) processing the extracted claims information and the defined events to create files containing event level information; 4) defining a time window for providing a timeframe from which to judge whether events should be considered in subsequent processing; 5) defining a set of variables as potential predictors; 6) processing the event level information, using the time window and the set of variables, to generate an analysis file; and 7) performing statistical analysis on the analysis file to generate a prediction model, said prediction model being a function of a subset of the set of variables.

Another aspect of the present invention involves a computer-implemented method for identifying, using the generated model, at risk patients diagnosed with congestive heart failure, said method comprising the additional step of applying the prediction model to a processed claims database to identify and output a file listing the likelihood of each patient having an adverse health outcome.

BRIEF DESCRIPTION OF THE DRAWINGS

The invention is best understood from the following detailed description when read in connection with the accompanying drawing, in which:

FIG. 2 is a high-level block diagram illustrating three exemplary sources of information suitable for use with the present invention.

FIG. 4 is a data structure diagram which shows an exemplary format for an event level file generated during the process shown in FIG. 1.

FIG. 6B is a time-line diagram which shows a first exemplary time window scheme suitable for use in processing the data, in part, from the event level files shown in FIG. 4.

DETAILED DESCRIPTION OF THE INVENTION

The present invention is embodied in apparatus and a method to identify, in a predetermined population of congestive heart failure patients, those patients at high risk of adverse health outcomes. The identification of these high risk patients being an initial stage in attempts, e.g., targeted interventions, to prevent and/or improve their health outcome.

Initially, one or more sources of information are used which allow for the identification of an initial population of congestive heart failure patients. Examples of sources include health care providers such as doctors, hospitals and pharmacies which all keep records for their patients. The individual records for each of these providers, however, may be scattered, difficult to access, and/or have many different formats.

On the other hand, a more comprehensive source containing this type of information exists in the health care claims records of any given benefits provider.

Figure 1A:
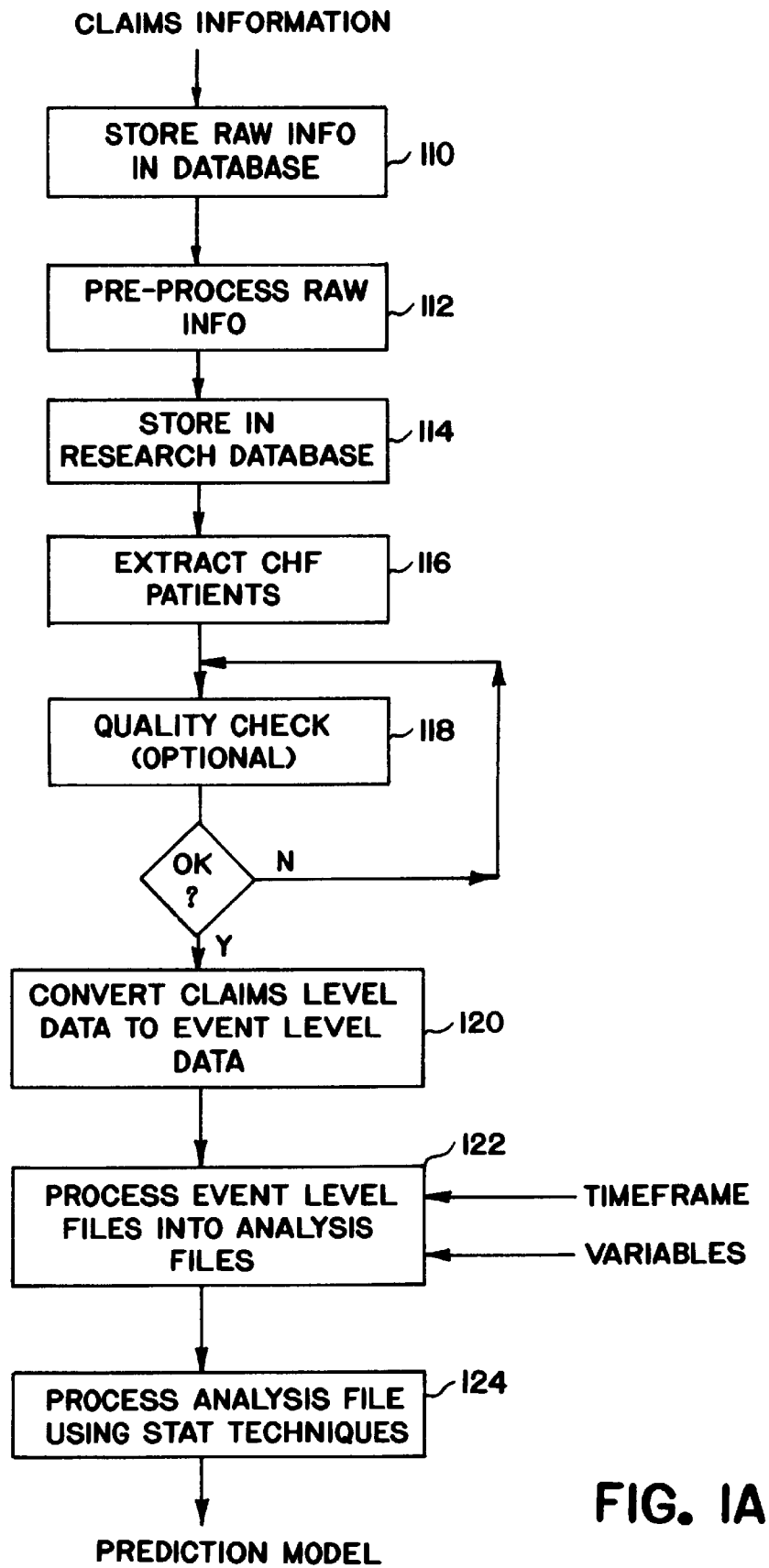
FIG. 1A is a high-level flowchart illustrating an exemplary overall process of the present invention.

Turning to the figures, FIG. 1A is a high-level flowchart illustrating an exemplary overall process of the present invention. As illustrated in FIG. 1, the "raw" claims information is received and stored in a database (e.g., DB2 format) represented by block 110. In the world of claims processing, before this database of "raw" information can be useful, some pre-processing, step 112, is generally performed which may include rejecting claims, reconciling multiple claims and so on. The output of this preprocessing step, represented by block 114, is a "cleaner" database now stored, in the exemplary embodiment, in SAS format.

SAS is a well known format and software package produced by SAS Institute, Inc. of Cary, N.C. It should be noted that other data processing and storage formats, as appreciated by those skilled in the art, could be used in the storage and processing of data.

It should also be noted that SAS formats, programming techniques and functions are more fully described in the SAS/STAT User's Guide, Version 6, Fourth Edition, Volumes 1 and 2, 1990 and the SAS Language: Reference, Version 6, First Edition, 1990 which are both herein incorporated by reference for their teachings regarding the SAS language, SAS programming, functions and formats.

Moreover, the SAS routines used for processing information as part of the present invention are used for computational operations, executed on a computer and stored on a storage medium such as magnetic tape, disk, CD ROM or other suitable medium for purposes of storage and/or transportability. The stored software can then be used with a computer such as a PC.

The claims records of the benefits provider, although containing important information, may not be organized in a manner for efficient analysis. Thus, the next step is to perform another processing step (e.g., screening for congestive heart failure patients, age, etc.), represented by block 116, to transform the "raw" data into a more appropriate and useful database. That is, the output data from the processing (i.e., extraction) step is a subset of the "raw" information and represents an initial universe of congestive heart failure patients upon which further processing is performed.

A next step, which is optional, is to perform a "quality check" on the initial universe of congestive heart failure patients. This step is somewhat subjective. This processing step, represented by block 118, using intermediate output files, performs a refinement of the extracted information by, for example, checking to see if an imbalance exists in the extracted information. This step, essentially a common sense check, can be performed as many times as necessary to ensure the integrity of the database data. At this point, the database data exists at the claim level.

The information existing at the claim level provides various information in the form of raw data elements. From the claims level data, the next processing step, represented by block 120, creates new files (e.g., primary file 1 and primary file 2) by reformatting the information into an event level format.

Before this occurs, a set of events (e.g., doctor visit for congestive heart failure) relevant to congestive heart failure are defined using a combination of both the raw data elements available from the claims information and clinical knowledge about congestive heart failure. With these events defined, the claims level information is used to create new files based on events rather than claims. Having the information in an event level format is an important aspect of the present invention in that, among other things, it allows for added flexibility in subsequent analysis.

As depicted by block 122, further processing is performed on the event level data to generate an analysis file. In particular, the processing is performed using input information representative of a sliding time window and a plurality of variables. The time window input limits the time periods in which the events from the primary files are considered. That is to say, the time window is used to identify an analysis region and a prediction region where activity in the analysis region is used to predict some predetermined outcome in the prediction region. The selection of variables, both dependent and independent, for analysis, is an important step impacting the accuracy of the final prediction model. The dependent variables are representative of the desired result (i.e., an adverse health outcome to be predicted); whereas, the independent variables are representative of predictors. This processing step, step 122, can be easily re-programmed, via the input parameters, for various time window adjustments as well as various variable modifications. The analysis file generated at this step is a member level file which means it is broken down by member.

With the analysis file in hand, a model or technique for identifying high risk subgroups is determined. That is, as represented by step 124, the analysis file is used to develop an identification technique represented by an equation incorporating a subset of the initial variables programmed into the above-mentioned processing step. The resulting subset are those variables which best reflect a correlation to adverse health outcomes, consequently, resulting in substantial use of health care resources (e.g., funds). It should be noted that the determination of the initial as well as the final variables is an important aspect of present invention as the variables may significantly impact the accuracy of the identification of the subgroup.

The above model for identification can be developed, step 124, in various ways using statistical techniques. The technique used in the exemplary embodiment of the present invention for generating the model is multiple logistic regression.

Figure 1B:
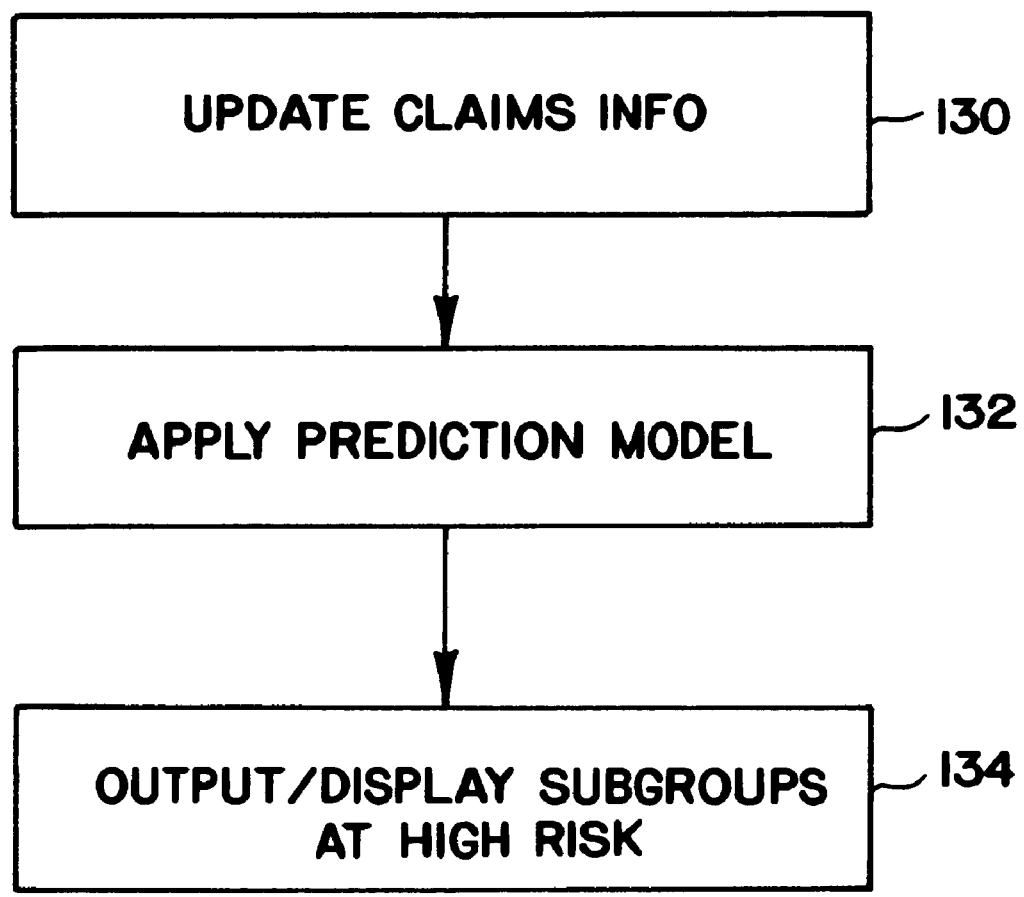
FIG. 1B is a high-level flowchart illustrating an exemplary process application for the present invention.

FIG. 1B is a high-level flowchart illustrating an exemplary process of the application of the present invention. Having developed the model, as shown in FIG. 1A, it can then be applied to updated claims data, step 132, or to other databases of congestive heart failure patients (e.g., claims information for other benefits providers), in order to identify at risk patients diagnosed with congestive heart failure, step 134, allowing for various types of targeted intervention to properly care for suffering patients as well as maximize the effective allocation of health care resources.

Exemplary Embodiment of the Invention

Although the present invention is illustrated and described below with respect to specific examples of a method and system for identifying congestive heart failure patients at high risk for adverse health outcomes, the invention is not intended to be limited to the details shown. Rather, various modifications may be made in the details within the scope and range of equivalents of the claims and without departing from the spirit of the invention.

As mentioned, the present invention is designed to identify patients with congestive heart failure at high risk of adverse health outcomes. The identification of this high risk subgroup being the first step in being able to try different treatment techniques (e.g., targeted interventions).

Initially, a source of information is required which allows for the identification of a population of congestive heart failure patients. A comprehensive source containing this type of information exists in the health care claims records of many benefit providers. As is known, claims for drugs, doctors and hospitals are received and processed for payment/reimbursement. In the exemplary embodiment of the present invention, this claims information is entered into a DB2 database on a benefits provider's computer system (not shown).

FIG. 2 is a high-level block diagram illustrating three exemplary sources of information suitable for use with the present invention. As illustrated in FIG. 2, the claims information of such a provider would typically include three sources: pharmacy claims (Rx) 210, doctor (DR) claims 212, and hospital (HL) claims 214. As listed on the blocks representing the claims information, many types of information would be available from the respective claims including drug codes, physician's names, diagnosis codes, procedures, various dates and other important information. Much of this information is referenced using codes, such as drug codes, procedure codes and illness codes. Appendices I–XIV provide exemplary listings of various codes used with the present invention. These codes were selected for processing purposes of the present invention from a voluminous source of codes and, as will be appreciated by those skilled in the art, may be modified to include/exclude codes deemed more/less useful at the various stages of processing.

It should also be noted that in the health care industry various codes are used in claims information for indicating which procedures, treatments, diagnoses, drugs, etc. are being claimed. For the exemplary embodiment of the present invention, the selected codes are shown in Appendices I–XIV. These codes were found in Physician's Current Procedural Terminology (CPT), American Medical Association (1995) and St. Anthony's ICD-9-CM Code Book (1994) which are both incorporated herein by reference for their teaching of codes and sources of codes. As will be appreciated by those skilled in the art, any set of codes, representative of the various procedures, treatments, diagnosis, drugs, etc. relevant for use with the present invention would suffice. Reference to such codes occurs throughout this specification.

The DB2 database represents a source of "raw" data elements which require processing. A first step in processing this raw data is to perform data integrity checks (e.g., rejected or reconciled claims). Subsequently, the data is routinely download into a "research" database. The research database is a claims level database in SAS format.

Figure 3:
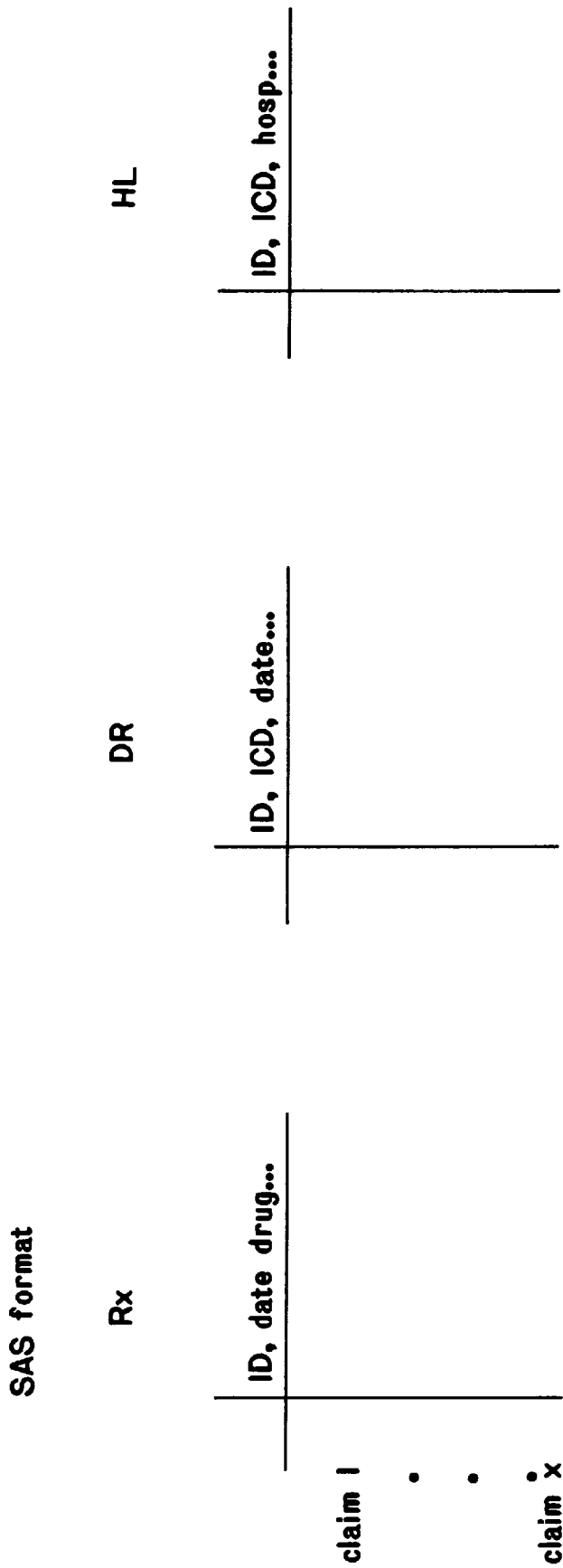
FIG. 3 is a data structure diagram which shows an exemplary format in which the information from the sources of FIG. 2 are stored in a research database.

Exemplary formats, for each of the Rx, DR and HL claims, of the records contained in the research Database, are shown in FIG. 3. As shown in FIG. 3, claims are listed from claim 1 to claim x and the appropriate information, for the particular service provider (e.g., Rx) being claimed, is also presented.

Once in SAS format, SAS procedures process the information to 1) identify patients with congestive heart failure (step 116), 2) process the claims level information into event level information (step 120), 3) using predetermined variables and timeframe schemes, generate analysis files for analysis purposes (step 122) and 4) create a prediction model as a function of those variables most reflective of the correlation to an adverse health outcome (step 124).

It should be mentioned that, from a statistical perspective, an important consideration in developing prediction models from datasets is sample size. To maximize the integrity of the prediction model, sample size is an important factor. Prevalence of congestive heart failure, as mentioned in the Background section, is reported to be approximately 1%; however, desirable sample sizes which may be used to determine prediction equations depend on the magnitude of association between variables. As these associations are initially unknown, all patients within any individual plan are initially included.

The first step, extracting patients with congestive heart failure (step 116), uses various parameters to define which patients qualify for the overall initial universe of CHF patients to be considered.

For example, in the exemplary embodiment of the present invention, only patients having 1) a continuous enrollment with the benefits provider of 6 months or longer and 2) having his/her first claim for CHF or treatment with CHF-related medication at 30 years old or older are eligible. Of course, these criteria are exemplary and could be modified such that 12 months or 3 months of enrollment is satisfactory or that an individual must be 18 years of age. In the exemplary embodiment of the present invention, the claims extraction step, step 116, extracts all claims data for patients with either an appropriate code for CHF (see Appendix I) or for treatment with an CHF-related drug (see Appendix XIV).

Subsequent to the claim extraction step, the claim adjustment and integrity checks are optionally performed, step 118. To do so, from the dataset defined above, intermediate output files are generated which contain information for processing purposes. In the exemplary embodiment of the present invention, information for the following items are generated for review to determine if the data within intermediate data files is in general agreement with the common clinical knowledge and experience and with literature evidence as to event frequencies.

A) First, a frequency count of the number of enrollment periods for the members is generated. Then, for members with multiple enrollment periods of at least 6 months duration, it is determined if a CHF diagnosis is present in each enrollment period. Consequently, enrollment periods without a CHF diagnosis are excluded and, for members with multiple enrollment periods that have a CHF diagnosis, only the most recent enrollment period that contains a CHF diagnosis is kept.

B) For the one enrollment period for all remaining members, ALL COSTS encountered by that member during the entire enrollment are identified. A complete proc univariate for ALL COSTS is provided for each plan separately and all plans together. It should be noted that "proc univariate" is a SAS procedure which generates descriptive statistics (e.g., mean, standard deviation, etc.)

C) From the ALL COSTS determined above, costs which are specifically cardiovascular (CV) COSTS are identified. In doing so, a cost is considered to be a CV COST, if a claim from the DR or HL file has any CV ICD-9 code in the first or second position. If a claim from the Rx file is from therapeutic class 04000 then it is counted as a CV claim and count cost as CV cost. A complete proc univariate for CV COSTS is also provided for each plan separately and all plans together.

D) From the CV COSTS, those costs which are specifically CHF COSTS are identified. A cost is considered to be CHF COST if a claim from the DR or HL file has any CHF ICD-9 code in the first or second position. A complete proc univariate for CHF COSTS is also provided for each plan separately and all plans together.

E) For all member enrollment periods remaining, the total member months for each plan is calculated separately and together. In doing so, a member is considered enrolled during any month that they were enrolled for at least one day. For this, a complete proc univariate is provided for member months for each plan separately and all plans together.

F) Finally, a unique member count is provided for all patient status code=20 within the remaining enrollment periods. It is noted that status code=20 indicates that the patient has expired or did not recover.

It should be noted that, regarding the cost calculations, the following guidelines apply in the exemplary embodiment of the present invention:

a. the cost of inpatient hospitalizations, emergency services, physician/outpatient, and other medical services on a per claim basis are considered to be:

AMTPAID+AMTCOPAY+AMTRESERVE+AMTDEDUCT b. the cost of drugs are considered to be:

AMTPAID+AMTCOPAY

It should also be noted that, for purposes of a cost heirachy, the following rules were used in the exemplary embodiment of the present invention.

1. Only hospitalizations for CHF can spawn other events.
2. Hospital costs include all Rx, procedure, physician charges.
3. Hospital visits can generate Rx and procedure events with costs set to zero (included in hospital cost).
4. Hospital visits cannot generate separate doctor visit events.

The above information for use in performing preliminary evaluations as to the integrity of the data is exemplary and could be modified to include/exclude parameters which are shown to be more/less useful within the spirit of the present invention.

With this information, a "quality check" is performed on the initial universe of CHF patients to make sure that the final results, i.e., prediction model, is not unreasonably skewed due to imbalanced input information. This processing step, block 118, using intermediate output files, allows for a refinement of the extracted information by, for example, checking to see if an imbalance exists in the extracted information which may otherwise taint the integrity of a prediction model. Step 118, in the exemplary embodiment, is performed manually by viewing the intermediate output files. It is contemplated, however, that using various threshold values, this information could be automatically processed to flag a potential imbalance.

Having now extracted and refined the claims level information according to various predetermined criteria deemed relevant for subsequent processing purposes, the information is converted into an event level format.

To provide processing flexibility, particularly in assigning time windows for analysis, the above-mentioned second step (i.e., converting the claims level information into event level information, step 122) is employed to generate two primary data files from which an analysis file can be created.

In the exemplary embodiment of the present invention, primary data file 1 is a member level file and contains all data of a static nature (i.e., not time sensitive) such as 1) Member Key, 2) Date of birth, 3) Gender, 4) First available date of enrollment (i.e., start of dataset or enrollment date), 5) End data of enrollment (i.e., end of dataset or last date of enrollment), 6) Date of first CHF diagnosis (ICD-9 code in any position), 7) Date of last CHF diagnosis (ICD-9 code in any position), 8) Date of first CHF hospitalization, 9) Date of last CHF hospitalization, 10) Date of first diabetes event (therapeutic class 081xxx OR ICD-9 code 250xx in any position), 11) Date of first dysrhythmia event (therapeutic class 047xxx OR ICD-9 codes 426xx–427xx in any position), 12) Date of first respiratory event (therapeutic class 151xxx OR ICD-9 codes 490xx–496xx in any position), 13) Date of patient status code=20.

Primary data file 2 is an events level file with a record for each event ordered by member and the chronological date of the event, in the present invention, presented in descending order of event date.

It should be noted that an event, sometimes referred to as an episode, is an occurrence which, based on clinical knowledge, is deemed relevant to CHF. Having knowledge of what raw data elements are available from the claims, a set of events is defined directly or indirectly from the data elements where events can be based on an individual data element, combination of data elements or derived from individual or multiple data elements.

FIG. 4 is an exemplary list of events and format for primary file 2 (an event level file).

With respect to FIG. 4, in the exemplary embodiment of the present invention, the following exemplary ground rules are established for providing counts for the various events:

I. Count as a HOSPITALIZATION event (using both 1st and 2nd ICD-9 codes) a claim having a from and through date of at least one day AND having a site code of 04. It is noted that a site code distinguishes between the sites at which the service under consideration took place (e.g., emergency room, doctor's office, etc.). It should be noted that costs go to 1st ICD-9 code category only. Also, if a new hospitalization occurs within one day of discharge from a previous hospitalization, the two hospitalizations are bridged into one. If a new hospitalization occurs greater than one day following a previous hospitalization, the second hospitalization is considered a new one.

II. Count as an ER VISIT event (using both 1st and 2nd ICD-9 codes) a claim having a site code of 07, 08 or 10 OR a claim with the following the Hospital Common Procedure Coding System (HCPCS) codes: A0010–A0070, A0215–A0225, A0999 with a provider code=81. It should be noted that costs go to 1st ICD-9 code category only.

III. Count as an OFFICE VISIT event (using only one ICD-9 code) a claim having a site code of 01 or 06 AND having a unique date of service (DOS) but allow for different provider keys on the same DOS (if same provider key on same DOS, consider to be the same office visit) BUT if an office visit event occurs during a hospitalization, do not generate an office visit event (Attribute all costs for this event to the hospitalization). ALSO count as an OFFICE VISIT a claim with the following HCPCS codes A0080–A0210 with provider code=81. For all other office visit events, costs go to 1st ICD-9 code category only. It should be noted that the following provider keys are not considered as separate office visits and should be bridged with an office visit that occurs on the same DOS if one exists: 1) 24 (therapeutic radiology), 2) 34, 35 (independent lab), 3) 55 (hosp o/pat lab x-ray).

The Three Event Types above are further defined according to the associated Diagnoses that follow:

Count as a Congestive Heart Failure (CHF) Hospital, Emergency Room (ER) or office visit if the first or second ICD-9 code is from Appendix I. Count as an Ischemic Heart Disease (IHD) Hospital, ER or office visit if (referring to Appendix II) a claim with one of the following ICD-9 codes in the first or second position:

| Subclass | Description |
|---|---|
| 1. 410xx | Acute myocardial infarction |
| 2. 411xx | Other acute and subacute forms of ischemic heart disease |
| 3. 412xx | Old myocardial infarction |
| 4. 413xx | Angina pectoris |
| 5. 414xx | Other forms of chronic ischemic heart disease |

Count as a Diabetes Hospital, Emergency Room or office visit if the first or second ICD-9 code is from Appendix III. Count as a Dysrhythmia Hospital, ER or office visit if the first or second ICD-9 code is from Appendix IV. Count as a Hypertension Hospital, ER or office visit if the first or second ICD-9 code is from Appendix V. Count as a Lifestyle Hospital, ER or office visit if the first or second ICD-9 code is from Appendix VI. Count as a Other Heart Disease Hospital, ER or office visit if the first or second ICD-9 code is from Appendix VII. Count as a Respiratory Disease Hospital, ER or office visit if the first or second ICD-9 code is from Appendix VIII. Count as a Thyrotoxicosis Hospital, ER or office visit if the first or second ICD-9 code is from Appendix X. Count as a Pulmonary Embolism Hospital, ER or office visit if the first or second ICD-9 code is from Appendix XI. Count as a Anemia Hospital, ER or office visit if the first or second ICD-9 code is from Appendix XII. Count as an Infection Hospital, ER or office visit if the first or second ICD-9 code is from Appendix XIII.

Count as an Other Disease Hospital, ER or office visit if the first or second ICD-9 code is not from any of the above Appendices.

Count as a MISCELLANEOUS MEDICAL EVENT any claim having a site code of 02, 03, 04, or 09 AND any claim that cannot be linked to one of the other type of events (ER, Hospitalital or Office Visit). In the exemplary embodiment of the present invention, subclasses of MISC. MED. EVENT include CV or NON-CV where: Count as a CV Miscellaneous event if the first or second ICD-9 code is from Appendix IX, and count as a Non-CV Miscellaneous event if the first or second ICD-9 code is NOT from Appendix IX.

Additionally, count as a Routine CV Procedure any claim with one of the following codes:

| | | |
|---|---|---|
| CPT | 80162 | Digoxin level |
| CPT | 80190 | Procainamide level |
| CPT | 80194 | Quinidine level |

The following procedures are desirably associated with a CV diagnosis from Appendix IX to be considered a Routine CV Procedure:

| | | |
|---|---|---|
| CPT | 80002–80019 | Automated blood tests |
| CPT | 93000–93014 | ECG related |
| CPT | 93040–93278 | ECG related |
| ICD-9 | 8951–8953 | ECG related |
| CPT | 93307–93350 | ECHO related |
| ICD-9 | 8968 | ECHO related |
| ICD-9 | 8972 | ECHO related |
| CPT | 71010–71035 | Chest radiology |
| ICD-9 | 8744–8749 | Chest X-ray |

Count as an Intermediate CV Procedure any claim with one of the following codes:

| | | |
|---|---|---|
| CPT | 71090 | Pacemaker |
| CPT | 93015–93024 | Stress Testing |
| CPT | 78460–78489 | CV radiology |
| CPT | 78401 78412 | (old codes for CV radiology) |
| CPT | 93501–93570 | Cardiac Cath |
| ICD-9 | 3721–3723 | Cardiac Cath |
| CPT | 93600–93660 | EPS |
| ICD-9 | 3726–3727 | EPS |
| CPT | 93720–93799 | Other |

Count as a Critical CV Procedure any claim with one of the following codes:

| | | |
|---|---|---|
| CPT | 92950–92996 | CPR, etc. |
| ICD-9 | 3791 | CPR, etc. |
| CPT | 33960–33978 | Cardiac assist |

Count as a CV Surgery any claim with one of the following codes:

| | | |
|---|---|---|
| CPT | 33010–33100 | Pericardial procedure |
| CPT | 33200–33261 | Pacemaker |
| ICD-9 | 3964 | Pacemaker |
| CPT | 33400–33492 | Valve surgery |
| ICD-9 | 35xx | Valve surgery |
| CPT | 33510–33560 | CABG |
| ICD-9 | 361x | CABG |
| ICD-9 | 360x | Angioplasty |
| CPT | 33600–33855 | Congenital mal. surgery |
| CPT | 33930–33950 | Heart (lung transplant |
| CPT | V421 | Heart transplant |
| ICD-9 | 375x | Heart transplantation |
| ICD-9 | 336x | Combined heart-lung transplantation |

It should be noted that the procedure cost is assigned to the ER, physician office visit or hospitalization in which the procedure occurred. If a procedure occurs outside of the assigned site codes for these events, consider the procedure to be a CV Miscellaneous medical event and assign the costs accordingly.

Regarding ACE inhibitor:
(a) ACE Inhibitor therapeutic class 045400
(b) Cost=0 if generated from a hospital claim.
(c) Category indicator=# ACE inhibitor Rx's in the month.

Regarding Loop Diuretic:
(a) Loop diuretic therapeutic class 043100
(b) Cost=0 if generated from a hospital claim.
(c) Category indicator=# of Loop diuretic rx's in the month.

Regarding Other Diuretic:
(a) Other diuretic therapeutic class 043200 and 043300
(b) Cost=0 if generated from a hospital claim.
(c) Category indicator=# of other diuretic rx's in the month.

Regarding Digoxin:
(a) Digoxin therapeutic class 041000
(b) Cost=0 if generated from a hospital claim.
(c) Category indicator=# of digoxin rx's in the month.

Regarding Beta Blocker:
(a) Beta Blocker therapeutic class 044000
(b) Cost=0 if generated from a hospital claim.
(c) Category indicator=# of beta blocker rx's in the month.

Regarding Calcium Channel Bockers:
(a) Calicum Channel Blocker therapeutic class 04200
(b) Cost=0 if generated from a hospital claim.
(c) Category indicator=# of calcium channel blocker Rx's in the month.

Regarding Other CV Drug:
(a) Other CV Drug therapeutic class 04000 (but not ther classes 041000, 042000, 043100, 043200, 043300, 044000, 045400)
(b) Cost=0 if generated from a hospital claim.
(c) Category indicator=# of other CV drug ix's in the month.

Regarding Non-CV Drug:
(a) Other Non- CV drug therapeutic class NOT 04000, 111200, 083000, 134000, OR 137000.
(b) Cost=0 if generated from a hospital claim.
(c) Category indicator=# of non-CV drug rx's in the month.

Regarding Na/H2O retention:
(a) Other Na/H2O retention (NSAID—ther class 111200, Steroids—ther class 083000, estrogens—ther class 134000 and 137000)
(b) Cost=0 if generated from a hospital claim.
(c) Category indicator=# of Na/H2O rx's in the month.

Figure 5:
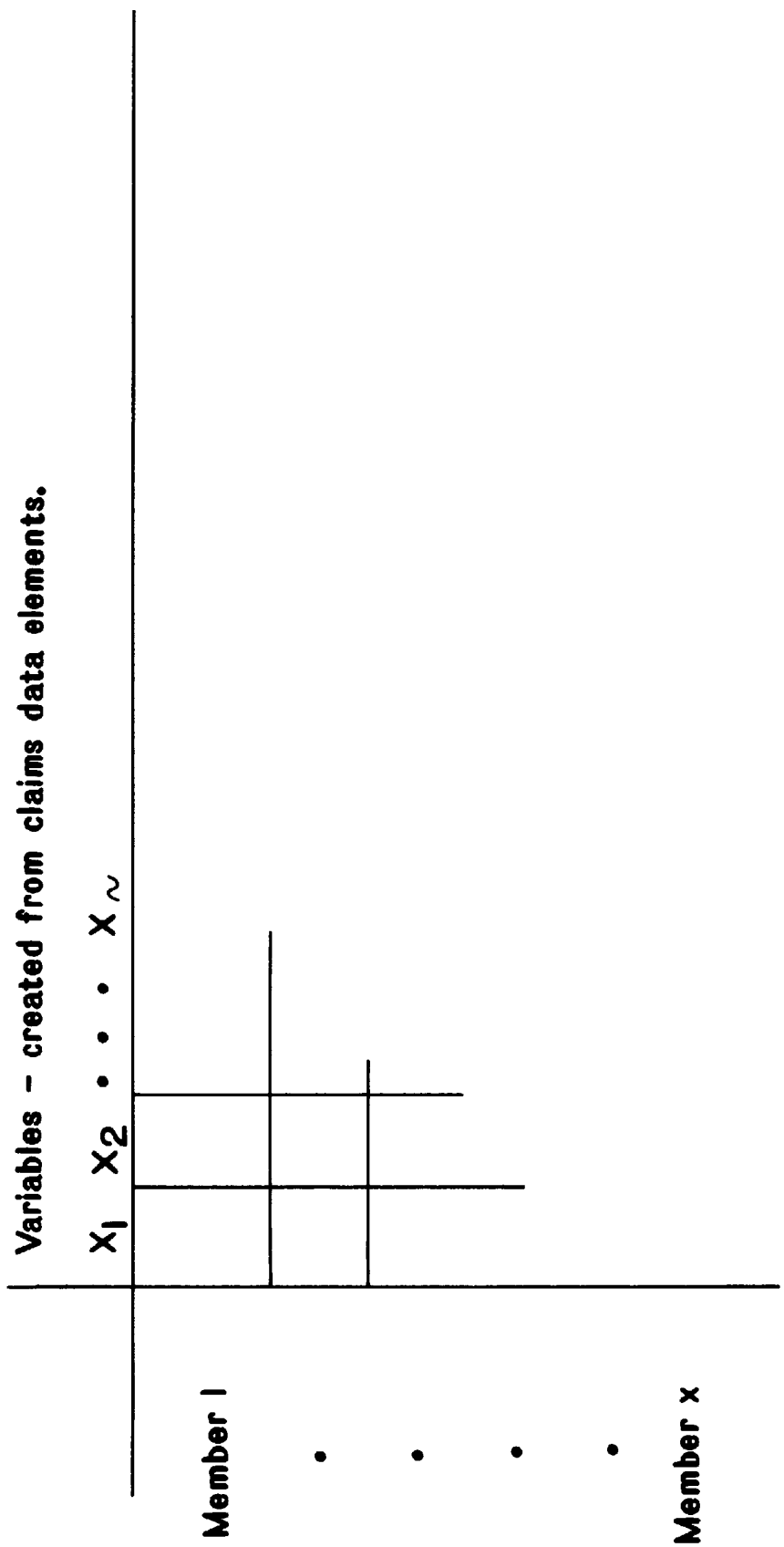
FIG. 5 is a data structure diagram which shows an exemplary format for an analysis file generated, in part, from the event level file shown in FIG. 4 and during the process shown in FIG. 1.

After generating the two primary files using the above described instructions and rules, corresponding to step 120 of FIG. 1, further processing is performed on the event level data to generate an analysis file, step 122. An exemplary format for the analysis file is shown in FIG. 5. As shown, the format of the analysis file includes a list of members in a first column of a table. Across the top of the table is a list of variables, described in detail below. And, the body of the table provides indications as to a member's relation to a listed variable.

In particular, the processing from the primary files to the analysis files includes an algorithm defined, in part, by a time window and a plurality of variables. The algorithm can be re-programmed for various time window adjustments as well as variable modifications. The analysis file generated at this step is a member level file (i.e., organized with respect to members). The main analysis files are member level files derived from the information in the primary files.

Each main analysis file is created to take into account a single reference time window of censored events and prediction window of interest for that file. Each new time window applied to the data, in the exemplary embodiment, uses another main analysis file.

To generate the analysis file, a time window scheme, using a plurality of variables, is applied to the event level data.

Discussing the variables first, included in the processing are both independent and dependent variables. The indepedent variables represent potential predictors of the adverse health outcomes; whereas, the dependent variables represent the adverse health outcome to be predicted.

To determine exemplary independent variables for step 122, as many of the original data elements as possible are used, assuming nothing about CHF. Then, based on clinical knowledge, additional variables are created. Furthermore, combinations of the data elements and/or variables, based on clinical knowledge, are used as variables. Finally, some variables may be created and used based on their potential utility as leverage points in disease management.

In the exemplary embodiment of the present invention, the plurality of variables, in addition to each of the items in the event file, currently used by step 122 in the SAS routine for generating an analysis file are shown below in Table 1. It is noted that each of the events in FIG. 4 are automatically considered an independent variable for processing.

Table 1
Additional Independent Variables of Interest:
1. Age (at time of 1st CHF diagnosis or drug therapy—one of the triple)
2. Gender (M/F)
3. HMO Membership (indetification of particular HMO)
4. Site of first CHF diagnosis (site code)
5. Ischemic Heart disease (Y/N)
6. Diabetes (Y/N)
7. Adverse Lifestyle Diagnoses (Y/N)
8. Cardiac Dysrhythmias (Y/N)
9. Other Heart Disease (Y/N)
10. Hypertensive Diseas (Y/N)
11. Number of Co-Morbid diseases (0-x)
12. Number of ACE inhibitor prescriptions (0-x)
13. Number of digoxin prescriptions (0-x)
14. Number of loop diuretic prescriptions (0-x)
15. Number of other CV prescriptions (0-x)
16. Number of non-V prescriptions (0-x)
17. Medication Possession Ratio (Compliance measure)
18. Number of CHF hospitalizations
19. Number of CHF emergency services 20. Number of physician office visits
21. Total Costs
 In-Patient Hospital Costs
 Emergency Room Costs
 Doctor Costs
 Pharmacy Costs
22. Cardiovascular Costs
 In-Patient Hospital Costs
 Emergency Room Costs
 Doctor Costs
 Pharmacy Costs
23. CHF Costs
 In-Patient Hospital Costs
 Emergency Room Costs
 Doctor Costs Turning to the dependent variables, potential dependent variables, for example, contemplated for use with the present invention as results to be predicted include:

1. Hospitalization (HL) for CHF. This is a dichotomous variable which is referred to as the HL indicator such that HL=1 if an admission occurred, otherwise the indicator equals 0.

2. High Cost. For example, the High Cost indicator may be defined as the highest 10% of resource utilization measured in dollars. Resources counted from time of cost in the top 10% of the first CHF diagnosis or receipt of first CHF-related drug (in the record +1, 3 and 6 months—separate analyses for each time period. Again, this is a dichotomous variable referred to as the High Cost indicator such that if the patient, for example, is in the top 10%, High Cost=1, otherwise High Cost=0.

The High Cost indicator, in the exemplary embodiment, could also be defined as the distribution of total cost per member (PMPM) in the prediction region (B to C). The High Cost indicator is set to 1 for the 10% of members with the highest PMPM in the Total Cost distribution and set to 0 for all others.

3. Death.

Although only three dependent variables are listed above, as those of ordinary skill in the art will appreciate, other known or yet unknown variables consistent with the goals of the present invention may also suitably serve as a dependent variable within the scope of the present invention.

Turning to the time window aspect of the generation of the analysis file, it should be noted that there is one analysis record for each selected member.

Figure 6A:
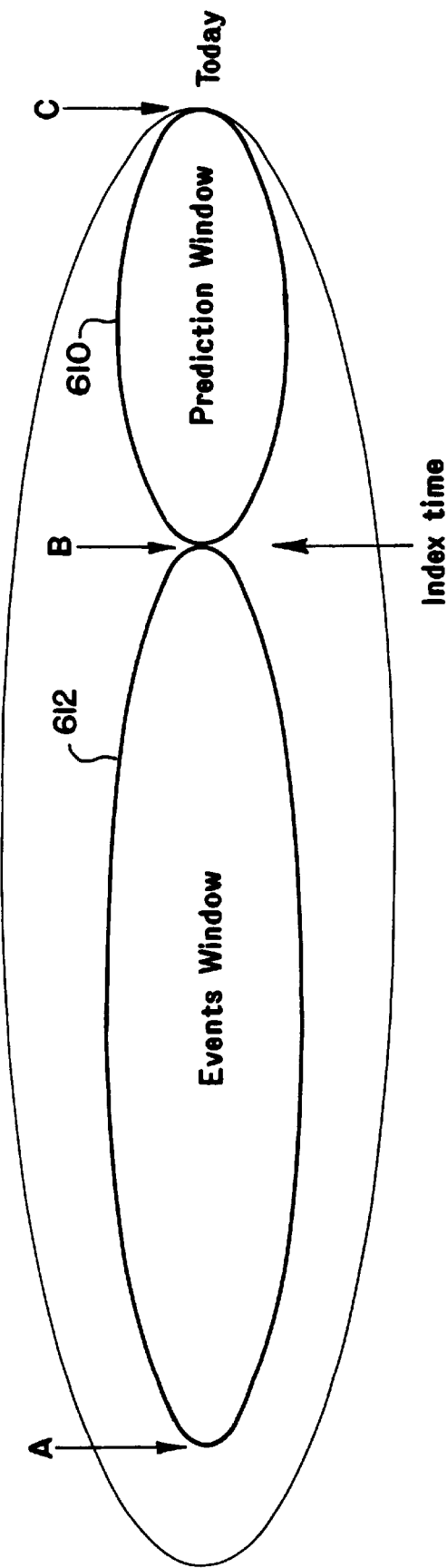
FIG. 6A is a simple bubble diagram illustrating the concept of analysis and prediction zones as used in the present invention.

In the present invention, a scheme, as described below, has been developed for defining prediction zones and censoring data to create the analysis file. That is, referring to FIG. 6A, a time window basically defines a prediction zone or region 610 and an events window (analysis region) 612 from where activity is used to predict something in the prediction zone. As those skilled in the art will appreciate, additional time window schemes may also adequately serve the present invention.

For purposes of explanation, the time that the claims history covers is referred to as the time window that starts at some point 'A' and ends at point 'C'. The time interval is divided into analysis and prediction regions by point 'B' such that A<B<C. That is to say, 'B' represents the present. 'A' represents the farthest past event and 'C' represents the farthest future event.

By way of example, Jane Doe's analysis record is based on claims from Jan. 1, 1991 through Jun. 30, 1993. Therefore, A=Jan. 1, 1991, C=Jun. 30, 1993 and B can be selected somewhere in between, such as Dec. 31, 1992. Generally, A is defined based on the data extraction protocol (i.e., from when the data is available) and C is defined by the last day for which the member is still enrolled and eligible for the benefits. Of course, variations of those general points of definition could be selected within the scope of the present invention.

The definition of the present instant B is important. In the subject invention, two basic definitions of B were devised in order to maximize the accuracy of the prediction model. Although, as would be understood by those skilled in the art, alternative definitions of B may also be used.

FIG. 6B is an exemplary time window scheme, referred to as Scheme 1, for use in processing the data from the event level files shown in FIG. 4.

In Scheme 1, the event prediction region is set from B to C such that B=C-(x# of months) for all the members in the analysis. For example, if a 6-month CHF hospitalization (HL) model (i.e., HL is used as a dependent variable) is to be built then B=C-(6 months). In Jane Doe's example, B would equal Dec. 31, 1992. Therefore, only data covering from A through B (Jan. 1, 1991–Dec. 31, 1992) is used to predict the CHF in the 'next 6 months'. The phrase 'next 6 months' in this context implies that the time point B is "NOW" and any time after it is in the FUTURE and any time before it is in the PAST. This is a key concept of Scheme 1 and is important to understanding the prediction model implementation and application.

In alternative embodiment, analysis weights which reflect proximity to the event to be predicted can be used, for example, within 3 months×1, 3–6 months×0.75, 6–9 months×0.5, 9–12 months×0.25, greater than 12 months× 0.125. Other suitable weighting techniques, as will be appreciated by those skilled in the art, such as negative weights could also be used. For example, in the exemplary embodiment of the present invention, the actual weighting factor used is $1/e-x$ where x=time in months from point B for each event.

Therefore, given a selected time window scheme and an appropriate set of predetermined variables, the processing step of 122 generates the analysis file.

Using the analysis file, the model for identification/prediction can then be developed in various ways using statistical techniques. In particular, the analysis file, now at a member level, is processed using statistical functions available in SAS. In the exemplary embodiment of the present invention, the statistical processing performed to generate the prediction model is multiple logistic regression. As will be appreciated by those skilled in the art, other statistical techniques may also be suitable for use with the present invention.

In the exemplary embodiment, the statistical processing, when applied to the analysis file, identifies variables which meet predetermined levels of significance (e.g., probability value<0.05). These variables then form a prediction model which is a mathematical equation of the following form:

Logit(p)=a+bx1+cx2 . . . +zxi where x1 . . . xi are the identified variables and a . . . z are there parameter estimates. An individuals probability (p) for the outcome under consideration is then determined using the following formula:

$$p = e\text{-logit}(p)/(1+e\text{-logit}(p)).$$

Using the above steps, several experiments were conducted. In one experiment, the results for a model based on Scheme 1, all commercial members and using the HL indicator as a dependent variable are listed below. The resulting independent variables, most likely to predict an adverse health outcome, were 1) hospitalization for CHF, 2) loop diuretics—days supply, 3) hospitalization for hypertension—length of stay, 4) doctor visits for CHF, 5) doctor visits for MI, and 6) ACE inhibitor possession (negative indicator).

In another experiment, the results for a model based on Scheme 1, all commercial members with no prior CHF hospitalization and using the HL indicator as a dependent variable are listed below. The resulting independent variables, most likely to predict an adverse health outcome, were 1) loop diuretics—days supply, 2) doctor visit for CHF, 3) hospitalization for IHD, 4) doctor visit for IHD, 5) emergency room visit for diabetes, 6) hospitalization for hypertension—length of stay, 7) emergency room visit for lifestyle, 8) hospitalization for other heart diseases, 9) doctor visit for pulmonary conditions, 10) doctor visit for anemia/emergency room visit for anemia, and 11) prescription (Rx) for "other" CV drugs.

In still another experiment, the results for a model based on Scheme 1, Medicaid members and using the HL indicator as a dependent variable are listed below. The resulting independent variables, most likely to predict an adverse health outcome, were 1) hospitalization for CHF, 2) loop diuretics—days supply, 3) doctor visits for CHF, and 4) emergency room visit for diabetes.

It should be noted that each of the experimental results indicate a different number of independent variables are used for the specific prediction models; and, depending on the precision of the models desired, more or fewer independent variables may be used based on their individual ability to accurately predict the selected dependent variable.

Next, the determined model is applied to the data. The determined model can be applied to the existing data, to the data as it is regularly updated or to other claims databases for other benefits providers. To do so, only the determined independent variables of interest need to be processed. Of course, as new claims databases are to be analyzed, the entire process can be repeated to generate a new model in order to determine if other variables may be better predictors. The output generated by applying the model is a file containing a list of all of the CHF patients ordered by an indicator representative of the likelihood that that patient will have an adverse health outcome (i.e., experience that defined by the dependent variable). This list can then be divided into subgroups such as in 5% or 10% increments of patients likely to have the adverse health outcome.

Model performance can now be assessed by determining the number of actual adverse health outcomes occurring in the prediction window for each 5% or 10% subgroup.

Applying the model to future claims data or other databases of CHF patients or building a new model in a new database as described above, CHF patients at high risk can be identified allowing for various types of intervention to maximize the effective allocation of health care resources for CHF patients. Such intervention may take the form of 1) specific case management, 2) novel interventions based on subgroup characteristics, 3) high risk intervention, 4) high (relative) cost intervention, or 5) plan modification all adhering, of course, to the best practice guidelines.

Appendices I–XIV follow.

APPENDIX I
CONGESTIVE HEART FAILURE DIAGNOSES ICD-9 CODES

| | |
|---|---|
| 398.91 | CHF with rheumatic fever, inactive |
| 402.01 | HTN heart dz with CHF, malignant |
| 402.11 | HTN heart dz with CHF, begnign |
| 402.91 | HTN heart dz with CHF, unspecified |
| 404.01 | HTN heart and renal dz with CHF, malignant |
| 404.03 | HTN heart and renal dz with CHF, and renal failure, malignant |
| 404.11 | HTN heart and renal dz with CHF, benign |
| 404.13 | HTN heart and renal dz with CHF, or renal failure, benign |
| 404.91 | HTN heart and renal dz with CHF, unspecified |
| 404.93 | HTN heart and renal dz with CHF, and renal failure, unspecified |
| 428xx | Heart Failure |

APPENDIX II

| | |
|---|---|
| 410xx | Acute myocardial infarction |
| 411xx | Other acute and subacute forms of ischemic heart disease |
| 412xx | Old myocardial infarction |
| 413xx | Angina pectoris |
| 414xx | Other forms of chromc ischemic heart disease |

APPENDIX III

Diabetes ICD-9 Codes

| | |
|---|---|
| 250xx | Diabetes mellitus |

DM Theruapeutic Class Codes

| | |
|---|---|
| 081100 | Insulin |
| 081200 | Oral hypoglycemic drugs |

APPENDIX IV
CARDIAC DYSRHYTHMIA CODES

Dysrhythmia ICD-9 Codes

| | |
|---|---|
| 426xx | Conduction disorders |
| 427xx | Cardiac dysrhythmias |

Dysrhythmia Therapeutic Class Codes

| | |
|---|---|
| 047100 | Class I- Membrane stabilizing |
| 047110 | Class Ia |
| 047120 | Class Ib |
| 047130 | Class Ic |
| 047300 | Class III |
| 047500 | Other antidysrhythmics |

APPENDIX V
HYPERTENSIVE DISEASE ICD-9 CODES

| | |
|---|---|
| 401xx | Essential hypertension |
| 402xx | Hypertensive heart disease |
| 403xx | Hypertensive renal disease |
| 404xx | Hypertensive heart and renal disease |
| 405xx | Secondary hypertension |

APPENDIX VI
ADVERSE LIFESTYLE ICD-9 CODES

| | |
|---|---|
| 2780x | Obesity |
| 303xx | Alcohol dependence syndrome |
| 3050x | Alcohol abuse |
| 3051x | Tobacco use disorder |
| 272xx | Lipid disorders |

APPENDIX VII
OTHER HEART DISEASE ICD-9 CODES

| | |
|---|---|
| 391xx | Rheumatic fever with heart involvement |
| 393–398xx | Chronic rheumatic heart disease |
| 421xx | Acute and subacute |
| 422xx | Acute myocarditis |
| 424xx | Valvular disorders (other diseases of endocrdium) |
| 425xx | Cardiomyopathy |
| 4290x | Myocarditis, unspecified |
| 4291x | Myocardial degeneration |
| 4292x | Cardiovascular disease, unspecified |
| 4293x | Cardiomegaly |

APPENDIX VIII
CHRONIC RESPIRATORY DISEASE ICD-9 CODES

| | |
|---|---|
| 490xx | Bronchitis, not specified as acute or chronic |
| 491xx | Chronic bronchitis |
| 492xx | Emphysema |
| 493xx | Asthma |
| 494xx | Bronchiectasis |
| 495xx | Extrinsic allergic alveolitis |
| 496xx | Chronic airway obstruction, not elsewhere classified |

APPENDIX IX
ALL CARDIAOVASCULAR DISEASE ICD-9 CODES

| | |
|---|---|
| 093–093x | Cardiovascular syphillis |
| 09883–09885 | Gonococcal heart disease |
| 27482 | Gouty tophi of heart |
| 3062 | Caardiovascular malfunctions arising from mental factors |
| 390–4299x | Diseases of the circulatory systems |
| 745–7469x | Anomolies of the heart |
| 785–7853x | Cardiovascular systems symptoms |
| 9971 | Cardiac complications |

APPENDIX X
THYROTOXICOSIS ICD-9 CODES

| | |
|---|---|
| 242xx | Thyrotoxicosis with or without goiter |

APPENDIX XI
PULMONARY EMBOLISM (PE) ICD-9 CODES

| | |
|---|---|
| 4151x | Pulmonaryembolism and infarction |

APPENDIX XII
ANEMIA ICD-9 CODES

| | |
|---|---|
| 280xx | Iron deficiency anemias |
| 281xx | Other deficiency anemias |
| 282xx | Hereditary hemolytic anemias |
| 283xx | Acquired hemolytic anemias |
| 284xx | Aplastic anemias |
| 285xx | Other and unspecified anemias |

APPENDIX XIII
INFEECTION ICD-9 CODES

| | |
|---|---|
| 001xx–139xx | Infectious and parasitic diseases |

APPENDIX XIV
CONGESTIVE HEART FAILURE DRUG THERAPIES

Double Therapies (therapeutic classes):

digoxin and loop diuretic (041000 and 043100)
digoxin and ACE inhibitor (041000 and 045400)
ACE inhibitor and loop diuretic (045400 and 043100)

Triple Therapy (therapeutic classes):

digoxin and loop diuretic and ACE inhibitor (041000 and 043100 and 045400)

What is claimed is:

1. A computer-implemented method for identifying at risk patients diagnosed with congestive heart failure, information about patients existing in a claims database, said method comprising the steps of:

processing, based on predetermined criteria, the patient information in the claims database to extract claims information for a group of congestive heart failure patients;

defining, using the information available in the claims database, a set of events relevant to congestive heart failure;

converting data representing the extracted claims information and the defined events into files containing event level information;

defining a time window to provide a timeframe from which to judge whether events should be considered in subsequent processing;

defining a set of variables as potential predictors;

processing the event level information, using the time window and the set of variables, to generate an analysis file; and performing statistical analysis on the analysis file to generate a prediction model for use in identifying at risk patients diagnosed with congestive heart failure, said prediction model being a function of a subset of the set of variables; and applying the prediction model to current data in the claims database to identify at risk patients for CHF.

2. The computer-implemented method of claim 1, wherein the step of processing extracts patients having been diagnosed with congestive heart failure or prescribed an anti-CHF drug.

3. The computer-implemented method of claim 1, wherein the step of defining a set of variables includes defining both dependent and independent variables and a hospital (HL) indicator is defined as a dependent variable, where independent variables are representative of predictors and the dependent variable is represenative of a adverse health outcome.

4. The computer-implemented method of claim 1, wherein the step of defining a set of variables includes defining both dependent and independent variables and a high cost indicator is defined as a dependent variable, where independent variables are representative of predictors and the dependent variable is representative of a adverse health outcome.

5. The computer-implemented method of claim 1 wherein the step of defining a set of variables includes defining both dependent and independent variables, substantially all of the data elements from the claims information, as well as at least one combination of data elements are used as independent variables.

6. The computer-implemented method of claim 1 wherein the step of performing statistical analysis includes performing logistic regression.

* * * * *